(12) United States Patent
Toh et al.

(10) Patent No.: US 6,172,140 B1
(45) Date of Patent: Jan. 9, 2001

(54) ACRYLIC THIO MONOMERS

(75) Inventors: Huan Kiak Toh, Fullarton; Fang Chen, Hallett Cove; Chong Meng Kok, Flagstaff Hill, all of (AU)

(73) Assignee: Sola International Holdings LTD, Scottsdale (AU)

( * ) Notice: Under 35 U.S.C. 154(b), the term of this patent shall be extended for 0 days.

(21) Appl. No.: 09/308,931

(22) PCT Filed: Dec. 3, 1997

(86) PCT No.: PCT/AU97/00816
§ 371 Date: Jul. 27, 1999
§ 102(e) Date: Jul. 27, 1999

(87) PCT Pub. No.: WO98/24761
PCT Pub. Date: Jun. 11, 1998

(30) Foreign Application Priority Data

Dec. 3, 1996 (AU) .................................................. 3958/96

(51) Int. Cl.[7] .............................. C08F 12/30; L08F 28/02
(52) U.S. Cl. .......................... 523/289; 526/286; 523/106; 558/251; 560/222
(58) Field of Search .............................. 524/547; 526/286, 526/289; 523/106, 173; 558/251; 560/222

(56) References Cited

U.S. PATENT DOCUMENTS

| 5,247,041 | * | 9/1993 | Iguchi et al. ........................ 526/289 |
| 5,384,379 | | 1/1995 | Bader et al. . |
| 5,488,128 | | 1/1996 | Bader et al. . |
| 5,741,831 | * | 4/1998 | Keita et al. ......................... 523/106 |

FOREIGN PATENT DOCUMENTS

| 82945/87 | 6/1988 | (AU) . |
| 63-188660 | 8/1988 | (JP) . |
| 2172969 | 7/1990 | (JP) . |
| 620249 | 7/1994 | (JP) . |
| 9132563 | 5/1997 | (JP) . |

* cited by examiner

Primary Examiner—Peter A. Szekely
(74) Attorney, Agent, or Firm—Burns, Doane, Swecker & Mathis, L.L.P.

(57) ABSTRACT

A cross-linkable polymeric casting composition includes an effective amount of an acrylic or methacrylic di- or polythiol monomer of the formula (1) wherein p is an integer of 0 or 1, M or M' are each spacer groups selected from one or more of the following formulae (i), (ii) wherein m is an integer of 0 or 1 and n is an integer of 0 to 3, with the proviso that m and n are not both equal to zero, $R^1 R^2$, $R^3$ and $R^4$, which may be the same or different, are selected from hydrogen, alkyl or substituted alkyl of 1 to 10 carbon atoms, alkoxy or substituted alkoxy of 1 to 10 carbon atoms, or $R^1$ or $R^2$ is (iii) and optionally a polymerisable comonomer.

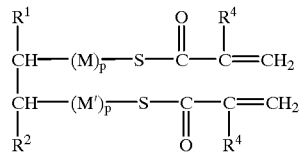

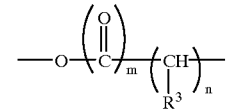

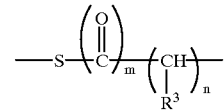

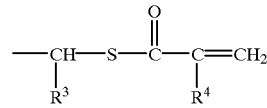

30 Claims, 5 Drawing Sheets

ACRYLIC THIO MONOMERS

Figure 1:
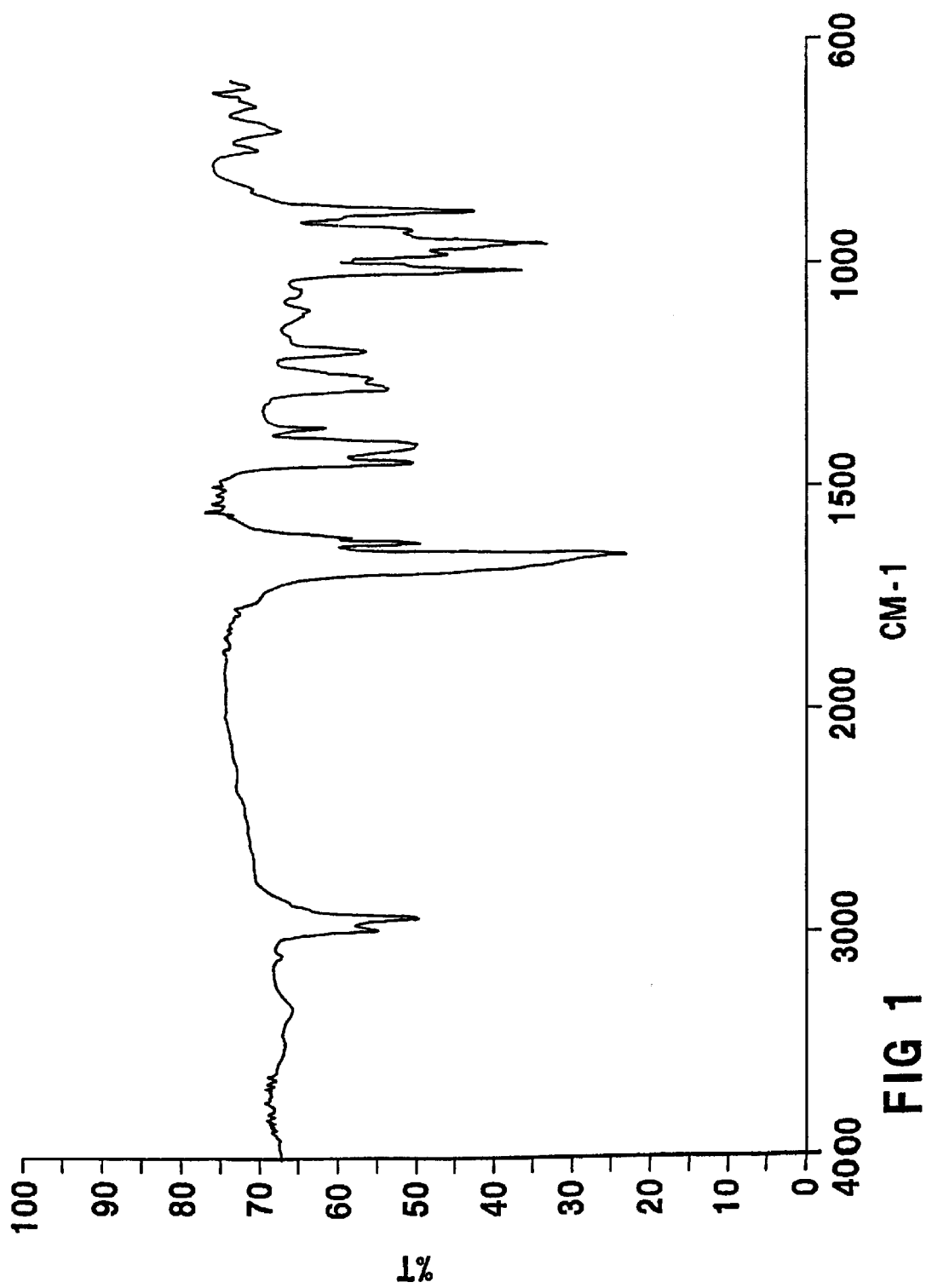

The present invention relates to the manufacture of plastic optical articles such as video discs and ophthalmic lenses.

The most widely used plastic ophthalmic lens material is polymerised diethylene glycol bis (allyl carbonate). This polymer has proved a satisfactory material for the manufacture of ophthalmic lenses because of a combination of features, including excellent transmission, resistance to discolouration, high strength and high impact resistance. The material has a reasonable abrasion resistance and can be coated to improve that resistance.

In Australian Patent Application 81216/87, the entire disclosure of which is incorporated herein by reference, applicant describes a cross-linkable casting composition including at least polyoxyalkylene glycol diacrylate or dimethacrylate and at least one poly functional unsaturated cross-linking agent. Whilst the lenses produced from the prior art compositions provide advances in the art, difficulties may be encountered in certain applications. For example, difficulties may be encountered in some patients in fitting lenses made from such compositions. Eye discomfort, including eye fatigue problems, may be encountered. Moreover, such lenses have been found to be cosmetically unattractive.

Further, in Australian Patent Application 75160/91, the entire disclosure of which is incorporated herein by reference, applicant describes a polyoxyalkylene glycol diacrylate or dimethacrylate; a monomer including a recurring unit derived from at least one radical-polymerisable bisphenol monomer capable of forming a homopolymer having a high refractive index of more than 1.55; and a urethane monomer having 2 to 6 terminal groups selected from a group comprising acrylic and methacrylic groups.

However, there remains a need in the prior art for optical articles of high refractive indices, high rigidity, very low densities and excellent colour, that still retain excellent mechanical properties.

Accordingly, it is an object of the present invention to overcome, or at least alleviate, one or more of the difficulties related to the prior art.

Accordingly, the present invention provides a cross-linkable polymeric casting composition including an effective amount of an acrylic or methacrylic di- or polythiol monomer of the formula

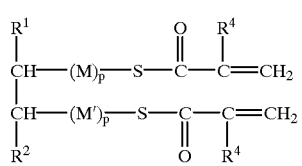

(1)

wherein p is an integer of 0 or 1

M and M' are each spacer groups selected from one or more of the following

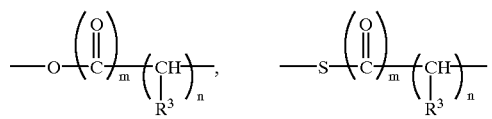

wherein m is an integer of 0 or 1 and n is an integer of 0 to 3, $R^1, R^2, R^3$ and $R^4$, which may be the same or different, are selected from hydrogen, alkyl or substituted alkyl of 1 to 10 carbon atoms, alkoxy or substituted alkoxy of 1 to 10 carbon atoms, or $R^1$ or $R^2$ is

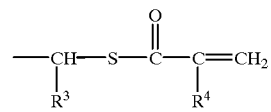

and optionally a polymerisable comonomer.

The casting composition may be heat and/or UV-curable, preferably UV curable.

A tri- or tetra- acrylic or methacrylic polythiol monomer is preferred.

The acrylic di- or poly-thiol monomer may be derived from a thiol selected from one or more of the following:

(a) 4-mercaptomethyl-3,6-dithia-1,8-octanedithiol [MDO]

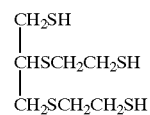

(b) Glycol Dimercaptoacetate

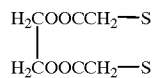

(c) Glycol Dimercaptopropionate Ethylene bis(3-Mercaptopropionate)

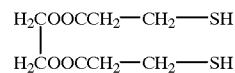

(d) 1,2,3-trimercaptopropane

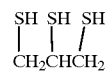

(e) 2-mercaptomethyl-2-methyl-1,3-propanedithiol

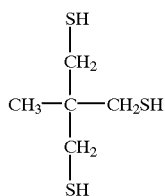

(f) 2,2-bis(mercaptomethyl)-1,3-propanedithiol

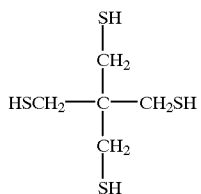

Preferably $R^3$ and $R^4$ are each hydrogen or methyl and one of $R^1$ and $R^2$ is

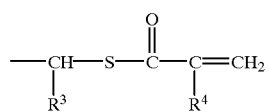

An illustrative example of an acrylic polythiol monomer is the trithiomethacrylate

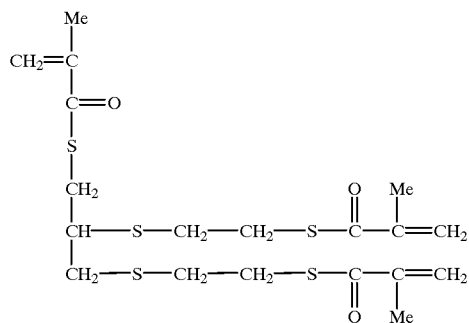

The optical article formed from the casting composition of the present invention may exhibit a refractive index in the high to very high -index range, low density and high rigidity.

By the term "high refractive index", as used herein, we mean a polymer having a refractive index of at least approximately 1.55, preferably 1.57. By the term "very high refractive index" as used herein, we mean a polymer having a refractive index of approximately 1.59 or above, preferably 1.60 or above.

By the term "low density", as used herein, we mean a density in the range of approximately 1.15 to 1.25 g cm$^{-3}$.

By the term "high rigidity" as used herein, we mean a polymer having a glass transition temperature (Tg) of at least approximately 65° C., preferably approximately 70° C., more preferably approximately 75° C. or above.

In a further aspect of the present invention, there is provided a method for preparing an acrylic or methacrylic di- or polythiol monomer of the formula

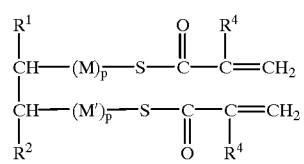

(1)

which method includes providing a di- or polythiol of the formula

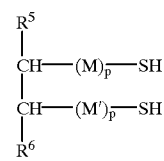

wherein
M and M' are each spacer groups as defined above,
p is an integer of 0 or 1,
$R^5$ and $R^6$, which may be the same or different, are selected from hydrogen, alkyl or substituted alkyl of 1 to 10 carbon atoms, alkoxy or substituted alkoxy of 1 to 10 carbon atoms,
or $R^5$ or $R^6$ is

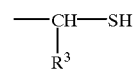

wherein $R^3$ is as defined above; and
reacting the di- or polythiol with an acrylic or methacrylic anhydride of the formula

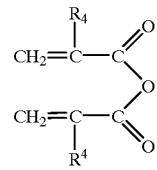

wherein $R^4$ is selected from hydrogen, alkyl or substituted alkyl of 1 to 10 carbon atoms, alkoxy or substituted alkoxy of 1 to 10 carbon atoms.

Where the acrylic thio monomer is a tri thio acrylate, the method according to the present invention may further include
further reacting the di- or polythiol with an acrylic or methacrylic salt of the formula

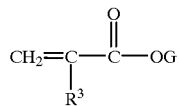

wherein G is an alkali metal selected from sodium (Na) or potassium (K).

The further reaction steps may be undertaken simultaneously with, or subsequent to, the first reaction step.

It has been found that the method according to this aspect of the present invention may produce the acrylic thio monomers in high yield.

As stated above, the cross-linkable polymeric casting composition may optionally further include a polymerisable comonomer.

The polymerisable comonomer may be selected to improve the properties and/or processability of the cross-linkable polymeric casting composition. The polymerisable comonomer may be selected to improve tint rate, hardness, abrasion resistance and the like of the resulting polymer. The polymerisable comonomer may be an unsaturated, thiol or epoxy comonomer. The polymerisable comonomer may be selected from any suitable type, e.g. methacrylates, acrylates, vinyls, vinyl ethers, allyls, epoxides, thiols and the like.

The polymerisable comonomer may preferably be selected from one or more of epoxidised monomer or oligomer, di- or polythiol, di- or poly vinyls, allylics, polyoxyalkylene glycol di-, tri-, tetra- and higher acrylates or methacrylates, polymerisable bisphenol monomers, urethane monomers having 2 to 6 terminal acrylic or methacrylic groups, fluorene acrylates or methacrylates, and thioacrylate or thiomethacrylate monomers.

The polymerisable comonomer, when present, may be present in amounts of from approximately 30 to 90% by weight, preferably approximately 35 to 80% by weight, most preferably approximately 40% to 70% by weight, based on the total weight of the casting composition.

Where an epoxidised monomer or oligomer is included, the epoxidised monomer may function to improve curing and casting characteristics. The epoxidised monomer or oligomer may fall into one or more of the following classes: internal, terminal, mono-functional, di-functional, tri-functional, tetra-functional, aliphatic, aromatic, cyclic, structurally simple, structurally complex, esters, ethers, amines. An epoxidised soybean material may be used. The epoxidised monomer or oligomer may be selected from one or more of the following Epoxidised soybean oil—Triglycerides of a mixture of epoxidised a) oleic acid, b) linoleic acid, c) linolinic acid Propylene Oxide Hexanediol diglycidyl ether (HDGE)

1,2 epoxy butane

Bisphenol fluorene diglycidyl ether (BPGE)

Epolight 100MF

AK-601

MY 721

The epoxidised monomer may be present in amounts of from approximately 0.001% to 10% by weight, preferably 0.01% to 5%, more preferably approximately 0.01% to 2%, based on the total weight of the casting composition.

Where a di- or polythiol comonomer is included, the di- or polythiol monomer may be of any suitable type. A di-, tri- or tetra polythiol compound may be used. A tri- or tetra-polythiol comonomer is preferred. The thiol comonomer may be selected from one or more of the following:

4-mercaptomethyl-3,6-dithia-1,8-octanedithiol [M DO]

Trimethylolpropane Tris (3-mercaptopropionate) [TTMP]

Pentaerythritol Tetrakis (3-mercaptoacetate) [PTMA]

Trimethylolpropane Tris (3-mercaptoacetate) [TTMA]

4-t-butyl-1,2-benzenedithiol

Bis(2-mercaptoethyl)sulfide 4,4'-thiodibenzenethiol benzenedithiol

Glycol Dimercaptoacetate

Glycol Dimercaptopropionate Ethylene bis(3-Mercaptopropionate)

Polyethylene Glycol Dimercaptoacetates

Polyethylene Glycol Di(3-Mercaptopropionate)

Pentaerythritol Tetrakis (3-mercapto-propionate) [PTMP]

Mercapto-methyl tetrahydrothiophene [MMTHT]

Tris-(3-mercaptopropyl)isocyanurate [TMPIC]

2-mercaptoethyl sulphide 1,2,3-trimercaptopropane 2,2-bis(mercaptomethyl)-1,3-propanedithiol Dipentaerythrithiol 1,2,4-trimercaptomethyl benzene 2,5-dimercaptomethyl-1,4-dithiane

BPHE-SH 4,8-bis(mercaptomethyl)-3,6,9-trithia-1,11-undecanedithiol 2-mercaptomethyl-2-methyl-1,3-propanedithiol DMDO: 1,8-dimercapto-3,6-dioxaoctane The polythiol comonomer is preferably pentaerythritol tetrakis (3-mercapto propionate) (PTMP) or trimethylolpropane tris (3-mercaptopropionate) (TTMP).

The thiol comonomer may preferably be present in amounts of from approximately 5 to 30% by weight, more preferably approximately 10 to 30% by weight, based on the total weight of the casting composition Where a vinyl comonomer is included, the vinyl comonomer may be selected from styrene, divinyl benzene, divinyl naphthene, substituted styrenes, 3,9-divinyl-2,4,8,10-tetraoxaspiro[5.5]undecane (DTU), a divinyl ester monomer of a bi- or polycyclic compound and mixtures and derivatives thereof.

The vinyl comonomer may preferably be present in amounts sufficient to provide rigidity and high index in optical articles formed from the casting composition, but not so much as to cause brittleness or low tintability. Amounts of from approximately 5 to 50% by weight, preferably approximately 15 to 40% by weight, more preferably about 20 to 30% by weight based on the total weight of the casting composition are preferred.

Where an acrylic or methacrylic monomer is included, the acrylic or methacrylic monomer may be selected from acrylates or methacrylate derivatives of a cycloolefin. An acrylate or methacrylate derivative of tricyclodecane is preferred.

A tricyclodecane dimethanol diacrylate or methacrylate is preferred.

A tricyclodecane dimethanol diacrylate or diacryloyl oxymethyl tricyclodecane of the following formula is preferred.

(DCPA)

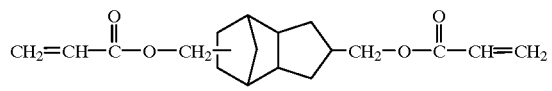

The acrylic or methacrylic monomer may alternatively or in addition be selected from highly rigid, high Abbe No. polyfunctional acrylates or methacrylates. Pentaerythritol tetracrylate (PTA) is a preferred example.

The acrylic or methacrylic monomer may be present in amounts sufficient to provide high Abbe number and high rigidity, but not so much as to cause brittleness or low tintability. Amounts of from approximately 5 to 25% by weight, preferably approximately 10 to 20% by weight, more preferably approximately 15 to 20% by weight, based on the total weight of the casting composition have been found to be suitable.

The urethane monomer, when present, may be a tetracyclic or higher urethane monomer.

Suitable materials falling within this definition include materials supplied under the trade names U4H, U-4HA and U-6HA by Shin Nakamura, NF-201 and NF-202 by Mitsubishi Rayon. U-4HA is preferred. These monomers may be included to improve physical toughness without causing the lens material to become too brittle. Impact resistance is improved without adversely affecting abrasion resistance.

The urethane monomer may be present in any suitable amount to provide a desired level of hardness. The urethane monomer may be present in amounts of from approximately 2.5 to approximately 25% by weight, preferably approximately 5 to 10% by weight based on the total weight of the casting composition.

Where a thiodiacrylate or dimethacrylate is included, the thiodiacrylate or dimethacrylates may be selected from bis(4-methacryloylthioethyl)sulfide (BMTES) and bis(4-methacryloylthiophenyl)sulfide (BMTS). The thioacrylate or methacrylate may be present in amounts of from 0 to approximately 20% by weight, preferably approximately 5 to 15% by weight, based on the total weight of the casting composition.

Where a fluorene diacrylate or dimethacrylate is included, the fluorene diacrylate or dimethacrylate monomer may be selected from a bisphenol fluorene dihydroxy acrylate (BFHA) or a bisphenol fluorene dimethacrylate (BFMA) or mixtures thereof.

The fluorene diacrylate or dimethacrylate monomer may be present in amounts of from 0 to approximately 20% by weight, preferably approximately 1 to 10% by weight.

The polyoxy alkylene glycol diacrylate or dimethacrylate compound according to the present invention, when present, may include ethylene oxide or propylene oxide repeating units in its backbone. A polyethylene glycol dimethacrylate is preferred. Suitable materials include dimethylacrylates where the number of repeating ethylene oxide groups is between 4 and 14. Suitable materials include those sold under the trade names NK Ester 4G, 6G, 9G or 16G. A 9G monomer is preferred.

The polyoxy alkylene glycol diacrylate or dimethacrylate component may be present in amounts of from 0 to approximately 20% by weight, preferably approximately 5% to 15% by weight, based on the total weight of the casting composition.

The high index bisphenol monomer component in the cross-linkable casting composition when present may be selected from: dimethacrylate and diacrylate esters of bisphenol A; dimethacrylate and diacrylate esters of 4,4"bishydroxy-ethoxy-bisphenol A and the like.

Preferred high index bisphenol compounds include bisphenol A ethoxylated dimethacrylate and tetra brominated bisphenol A ethoxylated dimethacrylates. A bisphenol A ethoxylate dimethacrylate sold under the trade designations ATM 20 by Ancomer or NS110 by Akzo have been found to be suitable.

The high index bisphenol monomer may be present in amounts of from 0 to approximately 45% by weight, preferably 5 to 40% by weight based on the total weight of the casting composition.

The cross-linkable casting composition according to the present invention may include a polymerisation curing agent.

The polymerisation curing agent may be a radical heat cationic or radical initiator. A radical heat initiator is preferred. The compositions may be cured by a combination of UV radiation and heat.

The amount of curing agent may vary with the monomers selected. It has been possible to operate with a relatively low level of curing agent of between approximately 0.05 and 1.5%, preferably 0.4% to 1.0% by weight.

The following curing agents have been found to be suitable.

AIBN (Azo radical heat initiator) Azodiisobutyronitrile

Trigonox TX-29 (Dialkyl Peroxide radical heat initiator) 1,1-di-(-butyl peroxy-3,3,5-trimethyl cyclohexane)

TBPEH (Alkyl Perester radical heat initiator) t-butyl per-2-ethylhexanoate (Diacyl Peroxide radical heat initiator) Benzoyl Peroxide (Peroxy Dicarbonate radical heat initiator) Ethyl Hexyl Percarbonate (Ketone Peroxide radical heat initiator) Methyl ethyl ketone peroxide Cyracure UV1-6974 (cationic photoinitiator) Triaryl sulfonium hexafluoroantimonate Lucirin TPO (radical photoinitiator) 2,4,6-Trimethylbenzoyldiphenylphosphine oxide Vicure 55 (radical photoinitiator) methyl phenylglycoxylate Bis(t-butyl peroxide) diisopropylbenzene t-butyl perbenzoate t-butyl peroxy neodecanoate Amicure DBU Amicure BDMA

DABCO

Amicure DBU and/or Amicure BDMA are preferred.

Initiator may be a single component or combination of initiator components.

Other additives may be present which are conventionally used in casting compositions such as inhibitors, dyes, UV stabilisers and materials capable of modifying refractive index. Mould release agents may be added. Such additives may include:

UV Absorbers Including

Ciba Geigy Tinuvin P—2(2'-hydroxy-5'-methyl phenyl) benzotriazole

Cyanamid Cyasorb UV 531-2-hydroxy-4-n-octoxybenzophenone

Cyanamid Cyasorb UV5411-2(2-hydroxy-5-t-octylphenyl)—benzotriazole

Cyanamid UV 2098—2 hydroxy-4-(2-acryloyloxyethoxy) benzophenone

National Starch and Chemicals Permasorb MA—2 hydroxy-4-(2 hydroxy-3-methacryloxy)propoxy benzophenone Cyanamid UV24—2,2'-dihydroxy-4-methoxybenzophenone BASF UVINUL 400—2,4 dihydroxy-benzophenone BASF UVINUL D-49—2,2'-dihydroxy-4,4' dimethoxy-benzophenone BASF UVINUL D-50—2,2', 4,4' tetrahydroxy benzophenone BASF UVINUL D-35-ethyl-2-cyano-3,3-diphenyl acrylate BASF UVINUL N-539-2-ethylhexyl-2-cyano-3,3-diphenyl acrylate Ciba Geigy Tinuvin 213
Hindered Amine Light Stabilisers (HALS), Including
Ciba Geigy Tinuvin 765/292—bis (1,2,2,6,6-pentamethyl-4-piperidyl) sebacate
Ciba Geigy 770—bis (2,2,6,6-tetramethyl-4-piperidinyl) sebacate Antioxidants including
Ciba Geigy Irganox 245—triethylene glycol-bis-3-(3-tertbutyl-4-hydroxy-5-methyl phenyl)propionate
Irganox 1010-2,2-bis[[3-[3,4-bis(1,1-dimethylethyl)4-hydroxyphenyl]-1oxopropoxy]methyl]-1,3-propanediyl 3,5-bis(1,1-dimethyl ethyl)-4-hydroxy benzene propanoate Irganox 1076—octadecyl 3-(3',5'-di-tert-butyl(-4'hydroxyphenyl) propionate
Anticolouring Agents Including
9, 10 dihydro-9-oxa-10-phosphaphenanthrene-1-oxide
Cure Modifiers Including
Dodecyl mercaptan
Butyl mercaptan
Thiophenol
Nitroso compounds such as Q1301 from Wako
Nofmer from Nippon Oils and Fats Other monomeric additives can be present in amounts up to 10% by weight as viscosity modifiers, and include monomers such as methacrylic acid, vinyl silanes, and other functional monomers. Other monomeric additives may be included to improve processing and/or material properties, these include:

methacrylic acid, maleic anhydride, acrylic acid
adhesion promoters/modifiers such as Sartomer 9008, Sartomer 9013, Sartomer 9015 etc.
dye-enhancing, pH-adjusting monomers like Alcolac SIPOMER 2MIM
a charge-reducing cationic monomer to render the material more antistatic, example Sipomer Q5-80 or Q9-75
mould release agents such as Phosphoric acid esters, e.g. octyl acid phosphate, etc, Alkyl quaternary ammonium salts, e.g. cetyl trimethyl ammonium bromide, etc., Zonyl Series, e.g. Zonyl FSO 100, Zonyl FSN 100, etc., Zelec Series, e.g. Zelec DP, Zelec UN, etc., and Unidain DS Series, e.g. DS 401, DS 202, etc.

The crosslinkable polymeric casting composition according to the present invention may be utilised in the preparation of an optical article. The optical article may be characterised by having an increased very high refractive index relative to known prior art articles. The optical article may exhibit excellent colour and low density.

In a preferred aspect of the present invention there is provided a method for preparing a polymeric article which method includes providing a cross-linkable polymeric casting composition including an effective amount of an acrylic or methacrylic di- or polythiol monomer of the formula

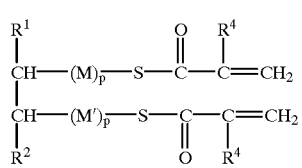

(1)

wherein
p is an integer of 0 or 1

M and M' are each spacer groups selected from one or more of the following

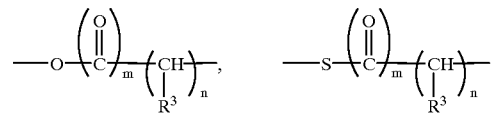

wherein m is an integer of 0 or 1 and n is an integer of 0 to 3, $R^1$, $R^2$, $R^3$ and $R^4$, which may be the same or different, are selected from hydrogen, alkyl or substituted alkyl of 1 to 10 carbon atoms, alkoxy or substituted alkoxy of 1 to 10 carbon atoms, or $R^1$ or $R^2$ is

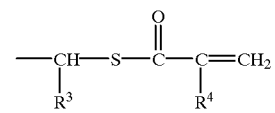

a heat and/or UV curing agent;
and optionally; a polymerisable comonomer. mixing the polymeric casting composition and curing agent; and subjecting the mixture to a cross-linking step.

The casting composition may be formed into a suitable article by mixing in a convenient vessel the components making up the material, and then adding the curing catalyst. The mixed material may then be degassed or filtered. As the curing time is substantially reduced, the casting process may be undertaken on a continuous or semi-continuous basis.

In a further aspect of the present invention there is provided a polymeric article prepared by the method as described above.

The polymeric article may be an optical article. The optical article may provide characteristics equal to or greater than those achievable with articles made from diethylene glycol bis(allyl carbonate) but with a considerably reduced cure time and substantially increased throughput.

The optical article may be an optical lens. The optical lens may be further characterised by having reduced weight and/or thickness relative to the prior art, excellent optical properties provided by the high rigidity, very low Yellowness Index and low density, whilst retaining good abrasion resistance and impact resistance.

The overall refractive index may be in the high to very high refractive index range of approximately 1.58 to 1.70, preferably 1.59 to 1.65.

The optical articles prepared by the method of this invention include camera lenses, ophthalmic lenses and video discs.

The chemicals 1,2-bis(2-mercaptoethyl thio)-3-mercaptopropane or 4-mercaptomethyl-3,6-dithia-1,8-octanedithiol are abbreviated to MDO.

The present invention will now be more fully described with reference to the accompanying examples. It should be understood, however, that the description following is illustrative only and should not be taken in any way as a restriction on the generality of the invention described above.

FIG. 1 Infrared spectrum of monomer MDO trithiomethacrylate in Example 1.

Figure 2:
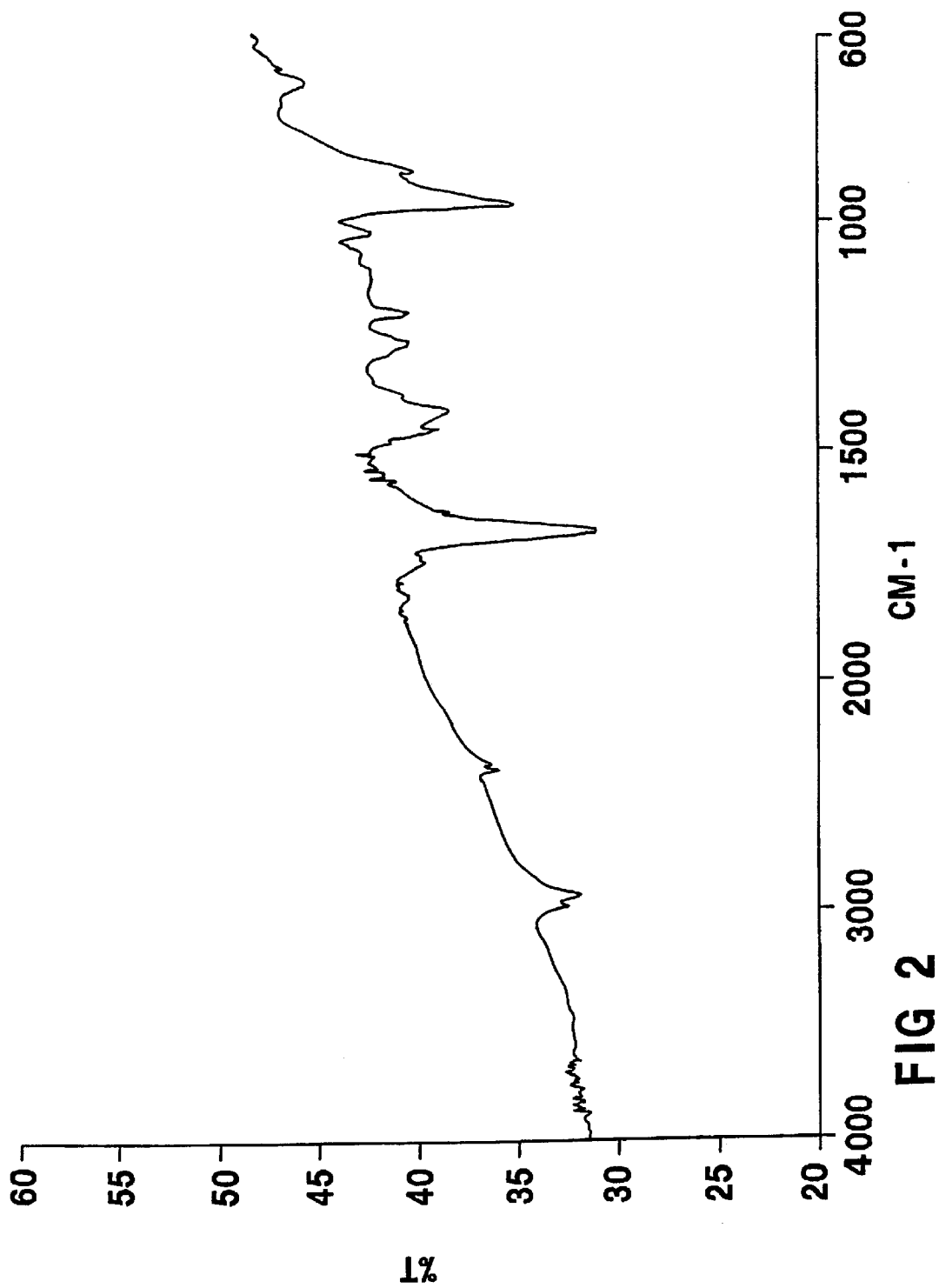

FIG. 2 Infrared spectrum of homopolymer for MDO trithiomethacrylate in Example 2.

Figure 3:
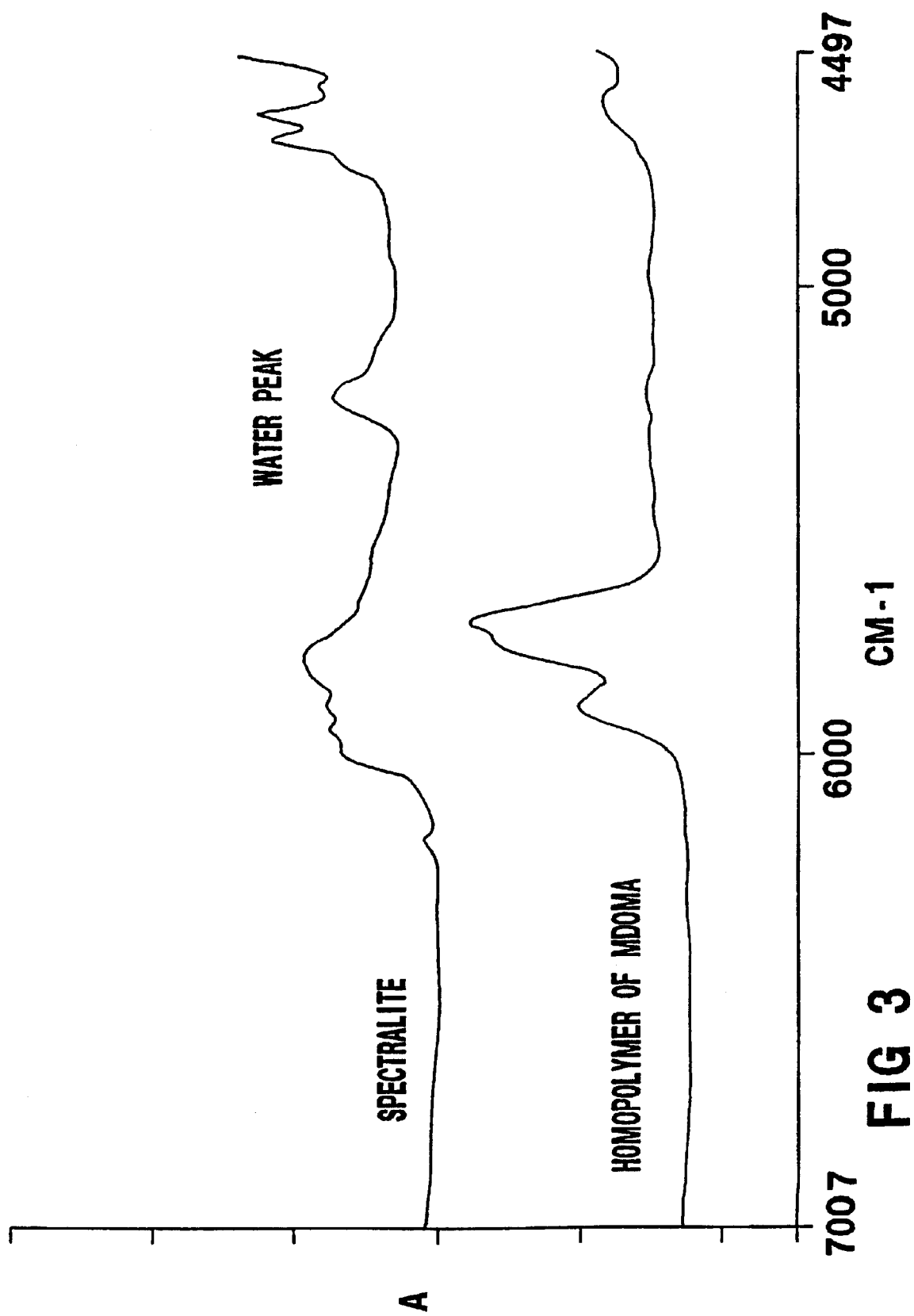

FIG. 3 The water uptake comparison of Example 2 material with that of commercial UV curable middle index material.

Figure 4:
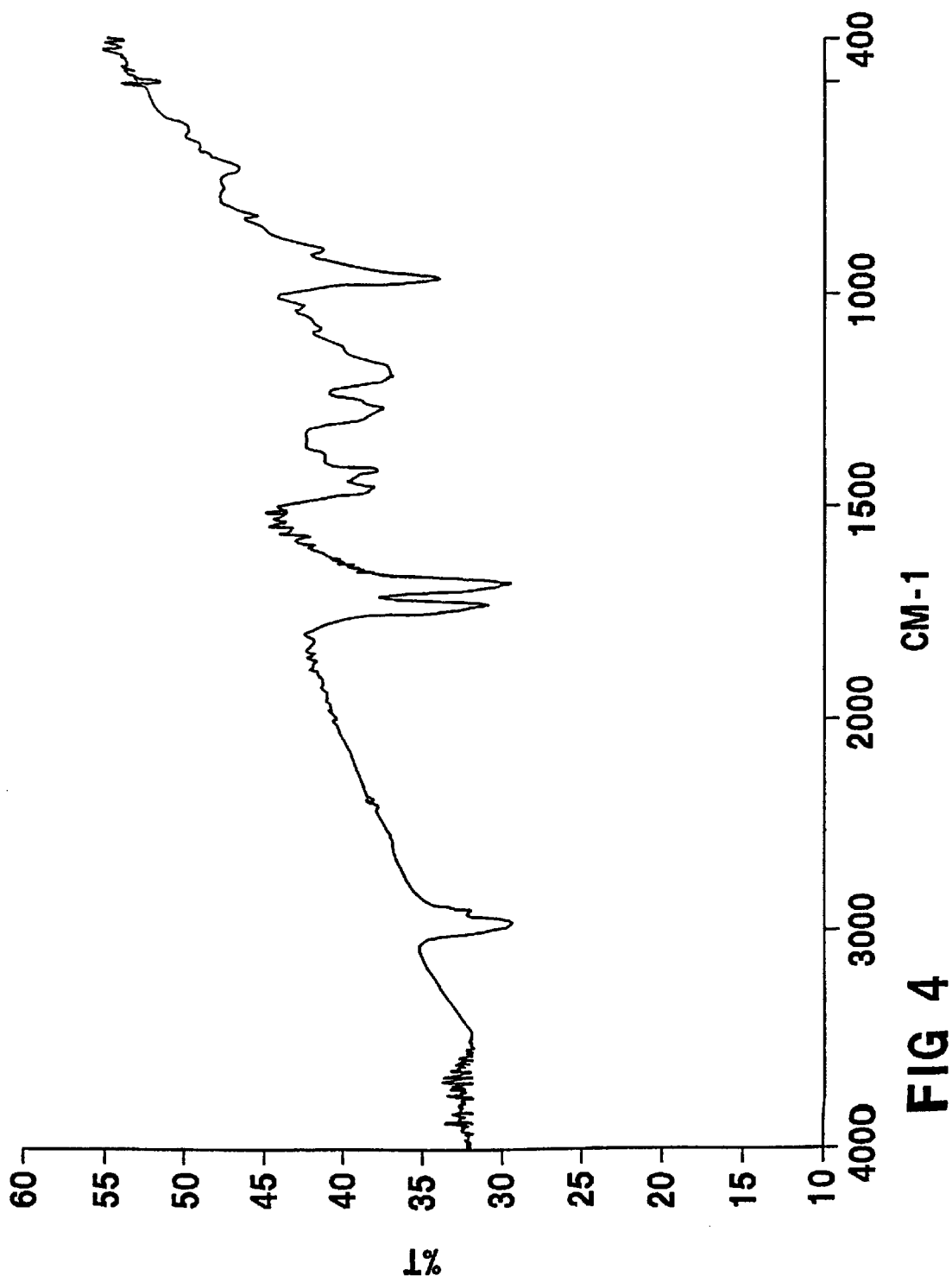

FIG. 4 Infrared spectrum of copolymer for MDO trithiomethacrylate and DCPA in Example 3.

Figure 5:
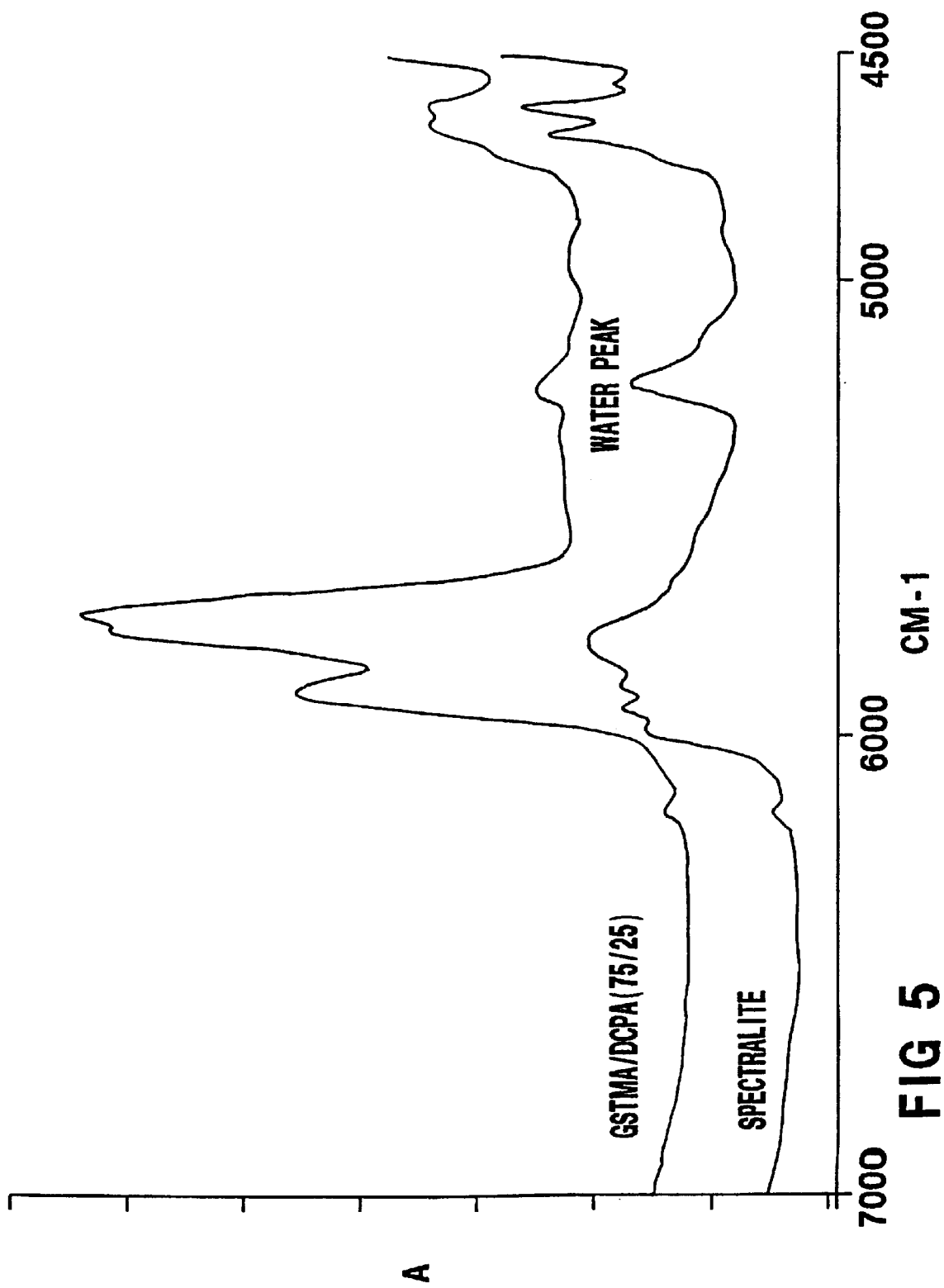

FIG. 5 The water uptake comparison of Example 3 material with that of commercial UV curable middle index material.

EXAMPLE 1

Preparation of MDO Trithiomethacrylate 20.8 g (0.08 ml) MDO dissolved into 100 ml 10% (w/w) NaOH aqueous solution was added into 400 ml methyl tert-butyl ether (MTBE) solution of 40.66 g (0.264 mol, 10% excess) methacrylic anhydride and 0.8 g 2,6-di-ter-butyl-methyl phenol (BHT) at 0° C. After adding the solution was stirred at 0° C. for further three hours. The organic layer was separated and washed successively with 200 ml 0.1% NaOH aqueous solution three times and NaCl saturated aqueous solution two times. Dried over anhydrous MgSO4, the solvent was removed, the remaining methacrylic anhydride in the product was removed by distillation or washing with methanol. After drying under vacuum, 30 g (80% yield) of colourless, clear viscous liquid was obtained. The infrared spectrum of this product is shown in FIG. 1.

EXAMPLE 2

The monomer synthesised in Example 1 was mixed with 0.8% (w/w) photoinitiator Vicure 55, then was used to fill the space between a pair of glass moulds separated by a plastic gasket at their periphery and held together by a clip. The mould was then passed two times (speed 55) under a UV lamp, kept at 100° C. for 45 minutes, passed another two times (speed 33) under UV lamp, then kept at 100° C. for one hour. Total curing time was about two hours. A clear, colourless and hard plastic was obtained. The infrared spectrum of this material is shown in FIG. 2. The properties of this homopolymer are summarised in Table 1. The water uptake is lower than that of commercial UV curable middle index material (FIG. 3)

TABLE 1

The properties of the material in Example 2

| MDOMA | Refractive Index | Abbe Number | Tg | Hardness (Bar-col) | Density |
|---|---|---|---|---|---|
| 100% | 1.635 | 37 | 68 | 30 | 1.31 |

EXAMPLE 3

The monomer synthesised in Example 1 was mixed with 25% DCPA and 0.8% (w/w) photoinitiator Vicure 55, then was used to fill the space between a pair of glass moulds separated by a plastic gasket at their periphery and held together by a clip. The mould was then passed two times (speed 55) under a UV lamp, kept at 100° C. for 45 minutes, passed another two times (speed 33) under UV lamp, then kept at 100° C. for one hour. Total curing time was about two hours. A clear, colourless and hard plastic was obtained. The infrared spectrum of this material is shown in FIG. 4. The properties of this homopolymer are summarised in Table 2. The water uptake is lower than that of commercial UV curable middle index material (FIG. 5).

TABLE 2

The properties of the material in Example 3

| MDOMA | DCPA | Refractive Index | Abbe Number | Tg | Hardness (Bar-col) | Density |
|---|---|---|---|---|---|---|
| 75% | 25% | 1.609 | 41 | 92 | 39 | 1.291 |

EXAMPLE 4

The monomer synthesised in Example 1 was mixed with 1% (w/w/) heat curing initiator TBPO, then was used to fill the space between a pair of glass moulds separated by a plastic gasket at their periphery and held together by a clip. The mould was then kept in an oven, the temperature of oven changed as following sequence, 35° C. in 5 hour, 35 to 60° C. in 9 hours, 60 to 85° C. in 3 hours, 85 to 110° C. in 2 hours, 110° C. for 2 hours, 110 to 80° C. in 5 minutes, 80° C. for 2 hours.

Total curing time was about 23 hours. A clear, colourless and hard plastic was obtained. The properties of this homopolymer are summarised in Table 3.

TABLE 3

The properties of the material in Example 4

| MDOMA | Refractive Index | Abbe Number | Tg | Hardness (Bar-col) | Density |
|---|---|---|---|---|---|
| 100% | 1.635 | 37 | 68 | 30 | 1.31 |

EXAMPLE 5

The monomer synthesised in Example 1 was mixed with 25 % (w/w) DCPA and 1% (w/w/) heat initiator TBPO, then was used to fill the space between a pair of glass moulds separated by a plastic gasket at their periphery and held together by a clip. The mould was then kept in an oven, the temperature of oven changed as following sequence, 35° C. in 5 hour, 35 to 60° C. in 9 hours, 60 to 85° C. in 3 hours, 85 to 110° C. in 2 hours, 110° C. for 2 hours, 110 to 80° C. in 5 minutes, 80° C. for 2 hours.

Total curing time was about 23 hours. A clear, colourless and hard plastic was obtained. The properties of this homopolymer are summarised in Table 4.

TABLE 4

The properties of the material in Example 5

| MDOMA | DCPA | Refractive Index | Abbe Number | Tg | Hardness (Bar-col) | Density |
|---|---|---|---|---|---|---|
| 75% | 25% | 1.609 | 41 | 92 | 39 | 1.29 |

EXAMPLE 6

The monomer MDOMA synthesised in Example 1 was formulated with different comonomers and UV cured using the method described in Example 2. The detailed formulations and the properties of the lenses were listed in Table 5.

TABLE 5

UV curable formulations with MDOMA and the properties of the lenses

| Composition and properties | Form. A | B | C | D | E | F | G | H | I | J | K | L |
|---|---|---|---|---|---|---|---|---|---|---|---|---|
| MDOMA | 65 | 60 | 55 | 50 | 50 | 55 | 50 | 50 | 40 | 30 | 20 | 10 |
| DCPA | 15 | 15 | 15 | 15 | 0 | 0 | 20 | 15 | 15 | 15 | 15 | 15 |
| NS110 | 5 | 10 | 15 | 20 | 40 | 25 | 20 | 20 | 10 | 40 | 50 | 60 |
| MDO | 10 | 10 | 10 | 10 | 10 | 10 | 10 | 10 | 30 | 10 | 10 | 10 |
| U4HA | 5 | 5 | 5 | 5 | 0 | 10 | 0 | 5 | 5 | 5 | 5 | 5 |
| Vicure 55 | 0.4 | 0.4 | 0.4 | 0.4 | 0.4 | 0.4 | 0.4 | 0.4 | 0.4 | 0.4 | 0.4 | 0.4 |
| % T | 89.4 | 89.5 | 89.6 | 89.7 | 89.3 | 89.3 | 89.3 | 89.3 | 89.9 | 90.0 | 90.1 | 90.5 |
| % Haze | 1.07 | 0.97 | 0.98 | 0.83 | 0.42 | 0.55 | 0.96 | 1.06 | 0.7 | 0.69 | 0.80 | 0.36 |
| YI | 1.42 | 1.24 | 1.36 | 1.32 | 1.09 | 1.16 | 1.54 | 1.45 | 1.37 | 1.36 | 1.27 | 1.27 |
| SG | 1.30 | 1.29 | 1.29 | 1.28 | 1.24 | 1.29 | 1.27 | 1.28 | 1.27 | 1.26 | 1.23 | 1.22 |
| Barcol | 51 | 46 | 51 | 50 | 46 | 50 | 49 | 50 | 45 | 43 | 43 | 39 |
| RI | 1.607 | 1.603 | 1.600 | 1.598 | 1.607 | 1.606 | 1.601 | 1.599 | 1.590 | 1.587 | 1.578 | 1.572 |
| Abbe | 39 | 39 | 39 | 39 | 36 | 35 | 38 | 38 | 39 | 39 | 38 | 38 |
| Tg ° C. | 100 | 100 | 105 | 104 | 91 | 97 | 95 | 97 | 104 | 97 | 97 | 93 |

NS110    Bisphenol A Ethoxylated Dimethacrylate
U4HA    Urethane Tetracrylate

Finally, it is to be understood that various other modifications and/or alterations may be made without departing from the spirit of the present invention as outlined herein.

What is claimed is:

1. A cross-linking polymeric casting composition including
   (A) an effective amount of an acrylic or methacrylic tri- or tetra-thiol monomer of the formula:

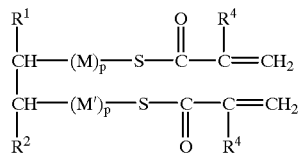

wherein
p is an integer of 0 or 1
M and M' are each spacer groups selected from one or more of the following

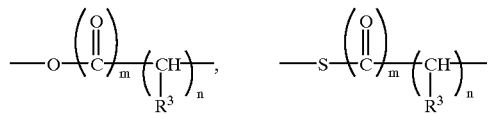

wherein m is an integer of 0 or 1 and n is an integer of 0 to 3, with the proviso that m and n are not both equal to 0 $R^1$ and $R^2$, which may be the same or different, are selected from hydrogen, alkyl or substituted alkyl of 1 to 10 carbon atoms, alkoxy or substituted alkoxy of 1 to 10 carbon atoms, or $R^5$ of the formula:

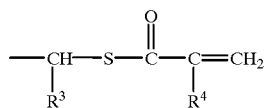

wherein at least one of $R^1$ and $R^2$ is $R^5$ and wherein $R^3$ and $R^4$, which may be the same or different, are selected from hydrogen and methyl; and
   (B) optionally a polymerizable comonomer.

2. A cross-linking polymeric casting composition according to claim 1, wherein the casting composition is UV curing.

3. A cross-linkable polymeric casting composition according to claim 2, wherein the monomer is derived from a thiol selected that is from the group consisting of 4-mercaptomethyl-3,6-dithia-1,8-octanedithiol, glycol dimercaptoacetate, glycol dimercaptopropionate, 1,2,3-trimercaptopropane, 2-mercaptomethyl-2-methyl-1,3-propanedithiol, 2,2-bis(mercaptomethyl)-1,3-propanedithiol, and mixtures thereof.

4. A cross-linkable polymeric casting composition according to claim 1 which includes the polymerizable comonomer that is selected to improve the properties and/or processability of the cross-linking casting composition, and is selected from one or more of the group consisting of methacrylates, acrylates, vinyls, vinyl ethers, allyls, epoxides and thiols.

5. A cross-linkable polymeric casting composition according to claim 4, wherein the polymerizable comonomer is selected from one or more of epoxidized monomer or oligomer, di- or polythiol, di- or poly vinyls, allylics, polyoxyalkylene glycol di-acrylates or methacrylates, polymerizable bisphenol monomers, urethane monomers having 2 to 6 terminal acrylic or methacrylic groups, fluorine acrylates or methacrylates, and thioacrylate or thiomethacrylate monomers.

6. A cross-linkable polymeric casting composition including
   (A) an effective amount of trithiomethacrylate having the formula:

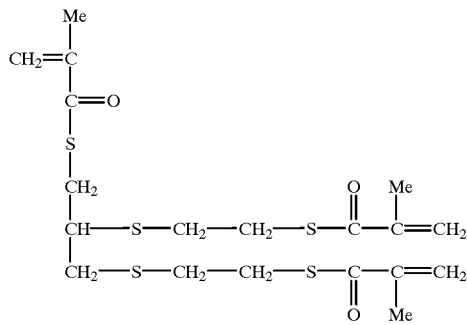

and
   (B) a polymerizable comonomer.

7. A cross-linking polymeric casting composition according to claim 6, wherein the casting composition is UV curing.

8. A cross-linkable polymeric casting composition according to claim 7, wherein the monomer is derived from a thiol selected that is from the group consisting of 4-mercaptomethyl-3,6-dithia-1,8-octanedithiol, glycol dimercaptoacetate, glycol dimercaptopropionate ethylene bis(3-mercaptopropionate), 1,2,3-trimercaptopropane, 2-mercaptomethyl-2-methyl-1,3-propanedithiol, 2,2-bis (mercaptomethyl)-1,3-propanedithiol, and mixtures thereof.

9. A cross-linkable polymeric casting composition according to claim 6 wherein the polymerizable comonomer is selected to improve the properties and/or processability of the cross-linking casting composition, and is selected from one or more of the group consisting of methacrylates, acrylates, vinyls, vinyl ethers, allyls, epoxides and thiols.

10. A cross-linkable polymeric casting composition according to claim 9, wherein the polymerizable comonomer is selected from one or more of epoxidized monomer or oligomer, di- or polythiol, di- or poly vinyls, allylics, polyoxyalkylene glycol di-acrylates or methacrylates, polymerizable bisphenol monomers, urethane monomers having 2 to 6 terminal acrylic or methacrylic groups, fluorine acrylates or methacrylates, and thioacrylate or thiomethacrylate monomers.

11. A method of preparing a polymeric article which method includes
(A) providing a cross-linking polymeric casting composition including
(i) an effective amount of an acrylic or methacrylic tri-or tetra-thiol monomer of the formula:

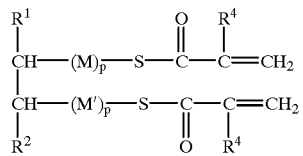

wherein
p is an integer of 0 or 1
M and M' are each spacer groups selected from one or more of the following

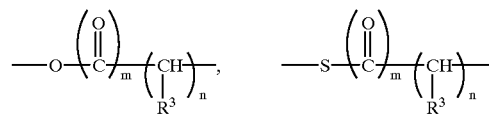

wherein m is an integer of 0 or 1 and n is an integer of 0 to 3, with the proviso that m and n are not both equal to 0 $R^1$ and $R^2$, which may be the same or different, are selected from hydrogen, alkyl or substituted alkyl of 1 to 10 carbon atoms, alkoxy or substituted alkoxy of 1 to 10 carbon atoms, or $R^5$ of the formula:

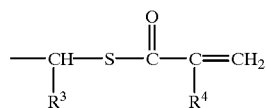

wherein at least one of $R^1$ and $R^2$ is $R^5$ and wherein $R^3$ and $R^4$, which may be the same or different, are selected from hydrogen and methyl;
(ii) a heat and/or UV curing agent; and
(iii) optionally a polymerizable comonomer; and
(B) mixing the polymeric casting composition and curing agent; and
(C) subjecting the mixture to a cross-linking step.

12. A method according to claim 11, wherein the casting composition is UV curing.

13. A method according to claim 12, wherein the monomer is derived from a thiol selected that is from the group consisting of 4-mercaptomethyl-3,6-dithia-1,8-octanedithiol, glycol dimercaptoacetate, glycol dimercaptopropionate, 1,2,3-trimercaptopropane, 2-mercaptomethyl-2-methyl-1,3-propanedithiol, 2,2-bis (mercaptomethyl)-1,3-propanedithiol, and mixtures thereof.

14. A method according to claim 11, wherein the casting composition includes the polymerizable comonomer that is selected to improve the properties and/or processability of the cross-linking casting composition, and is selected from one or more of the group consisting of methacrylates, acrylates, vinyls, vinyl ethers, allyls, epoxides and thiols.

15. A method according to claim 14, wherein the polymerizable comonomer is selected from one or more of epoxidized monomer or oligomer, di- or polythiol, di- or poly vinyls, allylics, polyoxyalkylene glycol di-acrylates or methacrylates, polymerizable bisphenol monomers, urethane monomers having 2 to 6 terminal acrylic or methacrylic groups, fluorine acrylates or methacrylates, and thioacrylate or thiomethacrylate monomers.

16. A method of preparing a polymeric article which method includes
(A) providing a cross-linking polymeric casting composition including
(i) an effective amount of trithiomethacrylate having the formula:

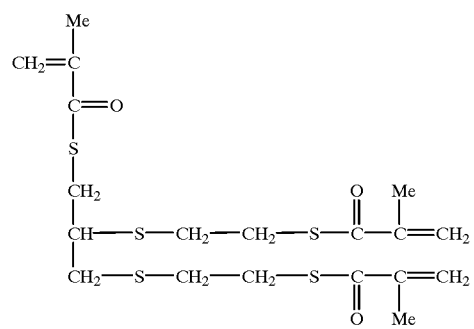

(ii) a heat and/or UV curing agent; and
(iii) a polymerizable comonomer; and
(B) mixing the polymeric casting composition and curing agent; and
(C) subjecting the mixture to a cross-linking step.

17. A method according to claim 16, wherein the casting composition is UV curing.

18. A method according to claim 17, wherein the monomer is derived from a thiol selected that is from the group consisting of 4-mercaptomethyl-3,6-dithia-1,8-octanedithiol, glycol dimercaptoacetate, glycol dimercaptopropionate, 1,2,3-trimercaptopropane, 2-mercaptomethyl-2-methyl-1,3-propanedithiol, 2,2-bis (mercaptomethyl)-1,3-propanedithiol, and mixtures thereof.

19. A method according to claim 16, wherein the polymerizable comonomer is selected to improve the properties and/or processability of the cross-linkable casting composition, and is selected from one or more of the group consisting of methacrylates, acrylates, vinyls, vinyl ethers, allyls, epoxides and thiols.

20. A method according to claim 19, wherein the polymerizable comonomer is selected from one or more of epoxidized monomer or oligomer, di- or polythiol, di- or poly vinyls, allylics, polyoxyalkylene glycol di-acrylates or methacrylates, polymerisable bisphenol monomers, urethane monomers having 2 to 6 terminal acrylic or methacrylic groups, fluorene acrylates or methacrylates, and thioacrylate or thiomethacrylate monomers.

21. An ophthalmic lens element formed from a crosslinking polymeric casting composition including (A) an effective amount of an acrylic or methacrylic tri-or tetra-thiol of the formula:

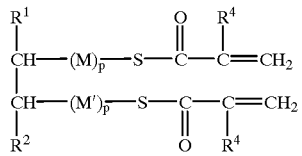

wherein
p is an integer of 0 or 1
M and M' are each spacer groups selected from one or more of the following

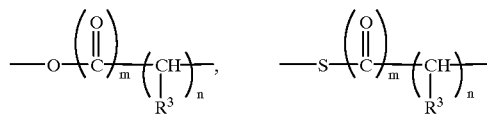

wherein m is an integer of 0 or 1 and n is an integer of 0 to 3, with the proviso that m and n are not both equal to 0 $R^1$ and $R^2$, which may be the same or different, are selected from hydrogen, alkyl or substituted alkyl of 1 to 10 carbon atoms, alkoxy or substituted alkoxy of 1 to 10 carbon atoms, or $R^5$ of the formula:

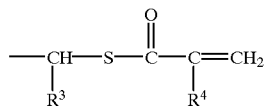

wherein at least one of $R^1$ and $R^2$ is $R^5$ and wherein $R^3$ and $R^4$, which may be the same or different, are selected from hydrogen and methyl; and (B) optionally a polymerizable comonomer; wherein the ophthalmic lens element has an overall refractive index in the range of approximately 1.58 to 1.70.

22. An ophthalmic lens element according to claim 21, wherein the casting composition is UV curing.

23. An ophthalmic lens element according to claim 22, wherein the monomer is derived from a thiol selected that is from the group consisting of 4-mercaptomethyl-3,6-dithia-1,8-octanedithiol, glycol dimercaptoacetate, glycol dimercaptopropionate, 1,2,3-trimercaptopropane, 2-mercaptomethyl-2-methyl-1,3-propanedithiol, 2,2-bis (mercaptomethyl)-1,3-propanedithiol, and mixtures thereof.

24. An ophthalmic lens element according to claim 21, wherein the casting composition includes the polymerizable comonomer that is selected to improve the properties and/or processability of the cross-linking casting composition, and is selected from one or more of the group consisting of methacrylates, acrylates, vinyls, vinyl ethers, allyls, epoxides and thiols.

25. An ophthalmic lens element according to claim 24, wherein the polymerizable comonomer is selected from one or more of epoxidized monomer or oligomer, di- or polythiol, di- or poly vinyls, allylics, polyoxyalkylene glycol di-acrylates or methacrylates, polymerizable bisphenol monomers, urethane monomers having 2 to 6 terminal acrylic or methacrylic groups, fluorene-acrylates or methacrylates, and thioacrylate or thiomethacrylate monomers.

26. An ophthalmic lens element formed from a crosslinking polymeric casting composition including (A) an effective amount of trithiomethacrylate having the formula:

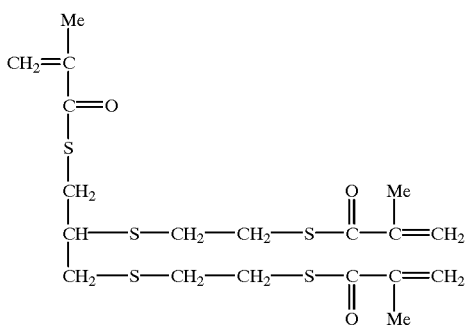

and (B) a polymerizable comonomer that includes an methacrylate derivative of a cycloolefin that comprises approximately 5 to 60% by weight of the casting composition; wherein the ophthalmic lens element has an overall refractive index in the range of approximately 1.58 to 1.70.

27. An ophthalmic lens element according to claim 26, wherein the casting composition is UV curing.

28. An ophthalmic lens element according to claim 27, wherein the monomer is derived from a thiol selected that is from the group consisting of 4-mercaptomethyl-3,6-dithia-1,8-octanedithiol, glycol dimercaptoacetate, glycol dimercaptopropionate, 1,2,3-trimercaptopropane, 2-mercaptomethyl-2-methyl-1,3-propanedithiol, 2,2-bis (mercaptomethyl)-1,3-propanedithiol, and mixtures thereof.

29. An ophthalmic lens element according to claim 26, wherein the polymerizable comonomer is selected to improve the properties and/or processability of the cross-linking casting composition, and is selected from one or more of the group consisting of methacrylates, acrylates, vinyls, vinyl ethers, allyls, epoxides and thiols.

30. An ophthalmic lens element according to claim 29, wherein the polymerizable comonomer is selected from one or more of epoxidized monomer or oligomer, di- or polythiol, di- or poly vinyls, allylics, polyoxyalkylene glycol di-acrylates or methacrylates, polymerizable bisphenol monomers, urethane monomers having 2 to 6 terminal acrylic or methacrylic groups, fluorine acrylates or methacrylates, and thioacrylate or thiomethacrylate monomers.

* * * * *

UNITED STATES PATENT AND TRADEMARK OFFICE
CERTIFICATE OF CORRECTION

PATENT NO. : 6,172,140 B1
DATED : January 9, 2001
INVENTOR(S) : Huan Kiak Toh et al.

It is certified that error appears in the above-identified patent and that said Letters Patent is hereby corrected as shown below:

<u>Title page,</u>
Item [73] Assignee, after the word LTD, delete "Scottsdale", insert -- Lonsdale --.

Signed and Sealed this

Twenty-fifth Day of December, 2001

Attest:

JAMES E. ROGAN
Attesting Officer     Director of the United States Patent and Trademark Office